(12) United States Patent
Chang

(10) Patent No.: US 7,673,533 B2
(45) Date of Patent: Mar. 9, 2010

(54) SAMPLING HEAD AND SAMPLING DEVICE FOR INTACT VEHICLE PAINT CHIPS IN FORENSIC APPLICATIONS

(76) Inventor: Wei-Tun Chang, 3F-6, No.76, Sikun 2nd Street, Banciao City, Taipei County 220 (TW)

( * ) Notice: Subject to any disclaimer, the term of this patent is extended or adjusted under 35 U.S.C. 154(b) by 455 days.

(21) Appl. No.: 11/730,591

(22) Filed: Apr. 3, 2007

(65) Prior Publication Data
US 2008/0245164 A1 Oct. 9, 2008

(51) Int. Cl.
*G01M 1/00* (2006.01)
(52) U.S. Cl. .................................. 73/864.41
(58) Field of Classification Search ............. None
See application file for complete search history.

(56) References Cited

U.S. PATENT DOCUMENTS

| | | | | | |
|---|---|---|---|---|---|
| 2,903,069 | A | * | 9/1959 | Lebourg et al. ............ 166/100 |
| 3,320,810 | A | * | 5/1967 | Stamulis et al. ........... 73/864.41 |
| 3,429,383 | A | * | 2/1969 | Pardue ............................ 175/4 |
| 3,732,725 | A | * | 5/1973 | Allen et al. ...................... 73/81 |
| 5,164,538 | A | * | 11/1992 | McClain, III ............... 102/517 |
| 5,212,991 | A | * | 5/1993 | Suzanne et al. ........... 73/863.11 |
| 5,398,587 | A | * | 3/1995 | Kornblith .................... 89/1.34 |
| 6,393,926 | B1 | * | 5/2002 | Bowersox et al. ........ 73/864.64 |
| 6,681,872 | B2 | * | 1/2004 | Radtke et al. ................. 175/20 |
| 2005/0044971 | A1 | * | 3/2005 | Harris ..................... 73/864.43 |

* cited by examiner

*Primary Examiner*—Robert R Raevis
(74) *Attorney, Agent, or Firm*—Rosenberg, Klein & Lee

(57) ABSTRACT

The present invention discloses a sampling head and a sampling device for intact vehicle paint chips for forensic applications, and the sampling head includes: a body being a non-metal cylindrical body and having a circular groove at the external periphery of the body, and an installing groove disposed axially at a front end of the body; at least one O-ring sheathed onto the circular groove and protruded slightly from the surface of the body; a metal head, embedded and fixed axially into the installing groove, and having a small portion protruded from the front distal surface of the body, and the metal head front distal surface has a groove; and a plastic layer, installed in a groove of the metal head, and an external lateral surface of the plastic layer is protruded from the front distal surface of the metal head to form a gluing surface for collecting a sample. In a sampling process, the sampling head is placed into a pneumatic sample pushing device, and the gun muzzle is attached onto the sampling paint position, and the internal compressed air in the air chamber injects the sampling head at the surface of a vehicle, and uses an instant dynamic force to touch and destroy the paint at the surface of a steel plate, plastic steel or plastic substrate of a car body to separate the substrate, and thus the sampling head will contain the removed sample containing the intact paint chip.

7 Claims, 7 Drawing Sheets

SAMPLING HEAD AND SAMPLING DEVICE FOR INTACT VEHICLE PAINT CHIPS IN FORENSIC APPLICATIONS

BACKGROUND OF THE INVENTION

1. Field of the Invention

The present invention relates to a sampling device provided for policemen or forensic scientists to collect intact paint chips from a vehicle to investigate the causes of the traffic accident. It is particularly a structure that uses a pneumatic method to shoot a sampling head and to form an instant pushing force. In the meanwhile, with the instant pushing force, the paint at the surface of various substrates including the steel, the plastic steel or the plastic plates was destroyed by the reaction force. And then an adhesive layer at the front distal surface of the sampling head was used to remove the intact paint chip.

2. Description of the Related Art

After a traffic accident, it is necessary for police officers to identify the cause based on using various evidences including skid marks, impact marks, transferred trace materials, such as glass and paint. To collect an intact paint chip as the standard sample on cite is a critical step for the complete examinations. Referring to FIG. 1, if a vehicle 90 hits another car, motorcycle or pedestrian, the surface of the car body will adhere some paints of the opposite party's vehicle, such as a collision at an external lateral area A at the front of the bumper or an area B at the car door. As a result, a wearing or a mark of the paint 91 of the opposite party's vehicle will remain, and such wearing or mark can be used for comparisons and identifications. Theoretically, standard samples of an intact paint structure including topcoat, primer, and/or putty layers at the surrounding of the collided positions of the vehicles of both parties should be collected. Since the automobile paint has a high adhesion with the steel plate, plastic steel or plastic materials of the car body, it is not easy to collect the intact paint sample at the aforementioned positions. At present, most investigators still use a sharp tool such as a razor blade to scrape the paint standard. However, the inventor of the novel invention fully understands that the paint scraped from the razor blade is mostly in a powder form based on the past working experience as a professor in central police university and a forensic investigator involving in paint examinations for 20 year in Taiwan. The powder type sample is unfavorable for analyzing and comparing the paint sample layer by layer, and thus all forensic laboratories have problems when using such samples.

SUMMARY OF THE INVENTION

In view of the foregoing shortcomings, the inventor of the present invention conducted extensive researches and experiments to develop a convenient and practical vehicle intact paint chip sampling equipment for police officers and forensic scientists in all of the world, in hope of overcoming the shortcomings of the prior art.

Therefore, the primary objective of this invention is to provide a sampling head and a sampling device used for generating a vehicle intact paint chip for the examination purpose. It simply requires users to pull a trigger to shoot the sampling head at a sample collecting area and instantly remove the intact paint chip and adhere the intact paint chip onto the sampling head automatically.

Another objective of the present invention is to maintain a steel plate or a body of the motor vehicle during the sample collecting process without damaging the steel plate or car body. It is not only to reduce any complaint but also to facilitate later identifications and comparisons, and the process is safe and free from hazards.

The technical characteristics of the present invention include a specially designed sampling head and a sample pushing device for shooting the sampling head wherein a gun-muzzle of the sample pushing device is sheathed with an elastic positioning disc for pressing against the surface of the vehicle. Meanwhile, the sampling head includes:

a) a body being a non-metal cylindrical body, the body having a circular groove disposed around the external periphery of the body and an installing bore disposed axially at a front end of the body;

b) at least one O-ring sheathed onto the circular groove and slightly protruded from the surface of the body;

c) a metal head embedded axially into the installing bore, the metal head having a small portion of the metal head protruded from a front distal surface of the body, a recess being disposed at the front distal surface of the metal head; and d) a plastic layer disposed in the recess of the metal head, an external lateral side of the plastic layer being protruded from the front distal surface of the metal head to form a gluing surface for collecting a sample.

DETAILED DESCRIPTION OF THE PREFERRED EMBODIMENT

Figure 1:
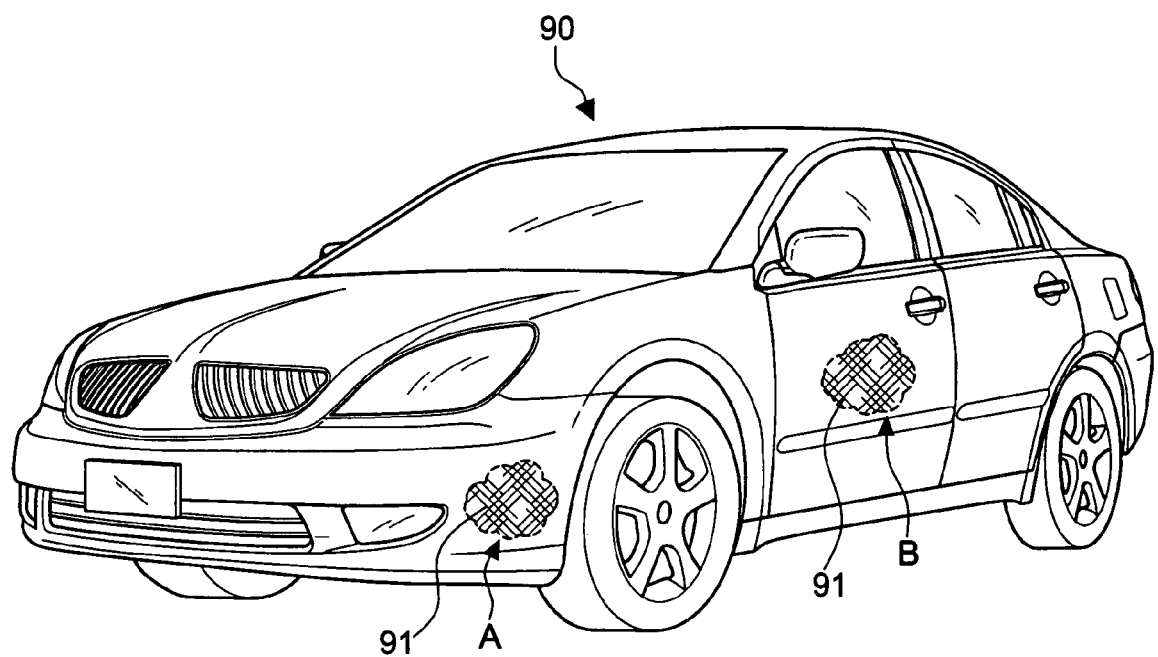
FIG. 1 is a schematic view of a vehicle after being hit in a prior art.
Figure 2:
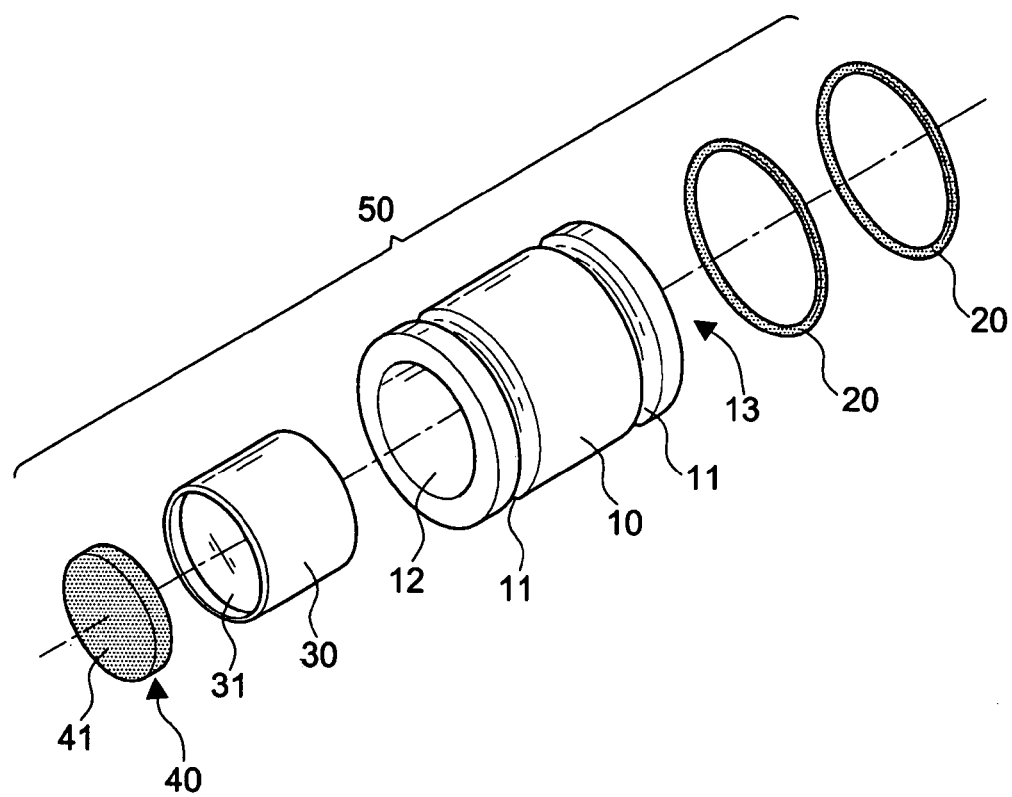
FIG. 2 is an exploded view of a sampling head of the present invention.
Figures 3, 4:
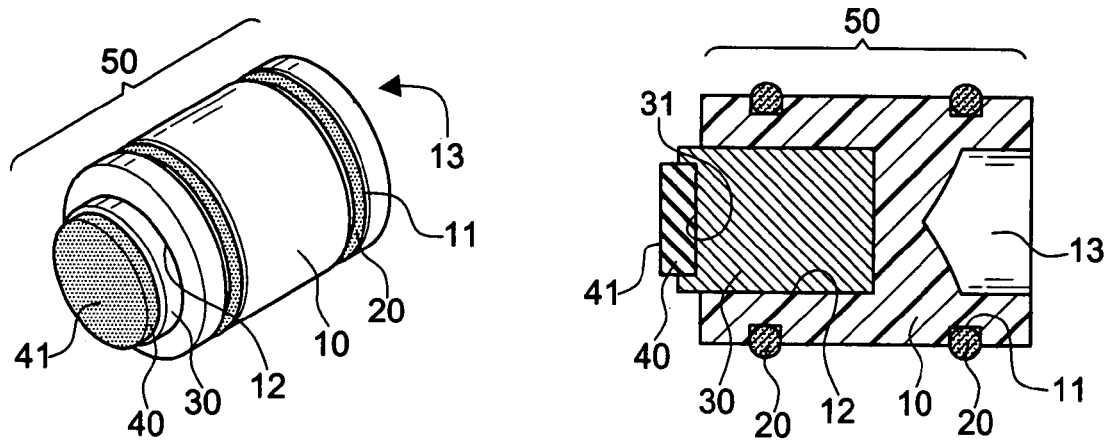
FIG. 3 is a perspective view of a sampling head of the present invention.
FIG. 4 is a cross-sectional view of a sampling head of the present invention.

Referring to FIGS. 2 to 4 for a sample head 50 in accordance with a preferred embodiment of the present invention, the sample head 50 comprises the following elements:

A body 10 is a non-metal cylindrical body preferably made of an industrial plastic material or ABS, but not limited to such arrangement. Metal materials are not used, due to the factors of its trajectory speed control, collision force, reduction of wearing at pipe walls and sampling capability. Experiments show that if the body is made of a metal including steel or lead, the sampling effect will be poor. Besides a sufficient collision force, a large penetration force is needed to damage the surface of the vehicle, such that a substantial indent, crack or break will be formed at the surface of the vehicle. Based on the consideration of safety, non-destructibility and selection of the shooting device, it is inappropriate to use a metal material for the body 10. Further, the external periphery of the body 10 includes a circular groove 11 for sheathing an O-ring 20, and the O-ring 20 is protruded slightly from the surface of the body 10. In this embodiment, there are two O-rings 20 and two circular grooves 11, but limited to such arrangement only. The purpose of the O-ring 20 is to keep the internal diameters of the body 10 and the shooting barrel 61 of the gun barrel 62 equal, and reduce the gap and increase the stability of the shooting range, and their effects will be described in detail later. In addition, a front end of the body 10 has an axial installing bore 12, and the installing bore 12 is preferably circular in shape, and the rear end of the body 10 has a cave 13.

A metal head 30 is embedded and fixed axially into the installing bore 12, and has a small portion protruded from a front distal surface of the body 10, and the front distal surface of the metal head 30 has a recess 31. The material of the metal head 30 can be iron, copper, lead, or other metal, or their alloys.

A plastic layer 40 is installed in a recess 31 of the metal head 30, and the external lateral surface of the plastic layer 40 is protruded from the front distal surface of the metal head 30 to form a gluing surface 41 for collecting a sample. The plastic layer 40 includes a double-sided tape such as the 3M tape, and preferably a foam with a thickness of 1 mm~4 mm. The invention is not limited to such arrangement, but any other equivalent material can be used to make the plastic layer 40, and an appropriate thickness and elasticity are necessary. Foam is an easily available material. For example, the depth of the recess 31 is equal to 1 mm, and the selected thickness of the foam can be 2 mm, wherein 1 mm of the thickness is glued into the recess 31, and another 1 mm of the thickness is protruded from the surface of the metal head 30.

In the foregoing technical characteristics, the following factors have been taken into consideration. The metal head 30 provides the required strength for the collision, and prevents the metal head 30 from being cracked, but it is not expected to hit the metal head 30 directly onto the surface of the motor vehicle, such that the steel plate will produce a serious indent. Now, the plastic layer 40 will be able to provide a buffer effect to prevent the steel plate of the vehicle from being indented or deformed. In addition, the body 10 of the sampling head 50 of the invention has a feature similar to a piston, and such arrangement has considered its application to fit the sample pushing device 80.

Figure 5:
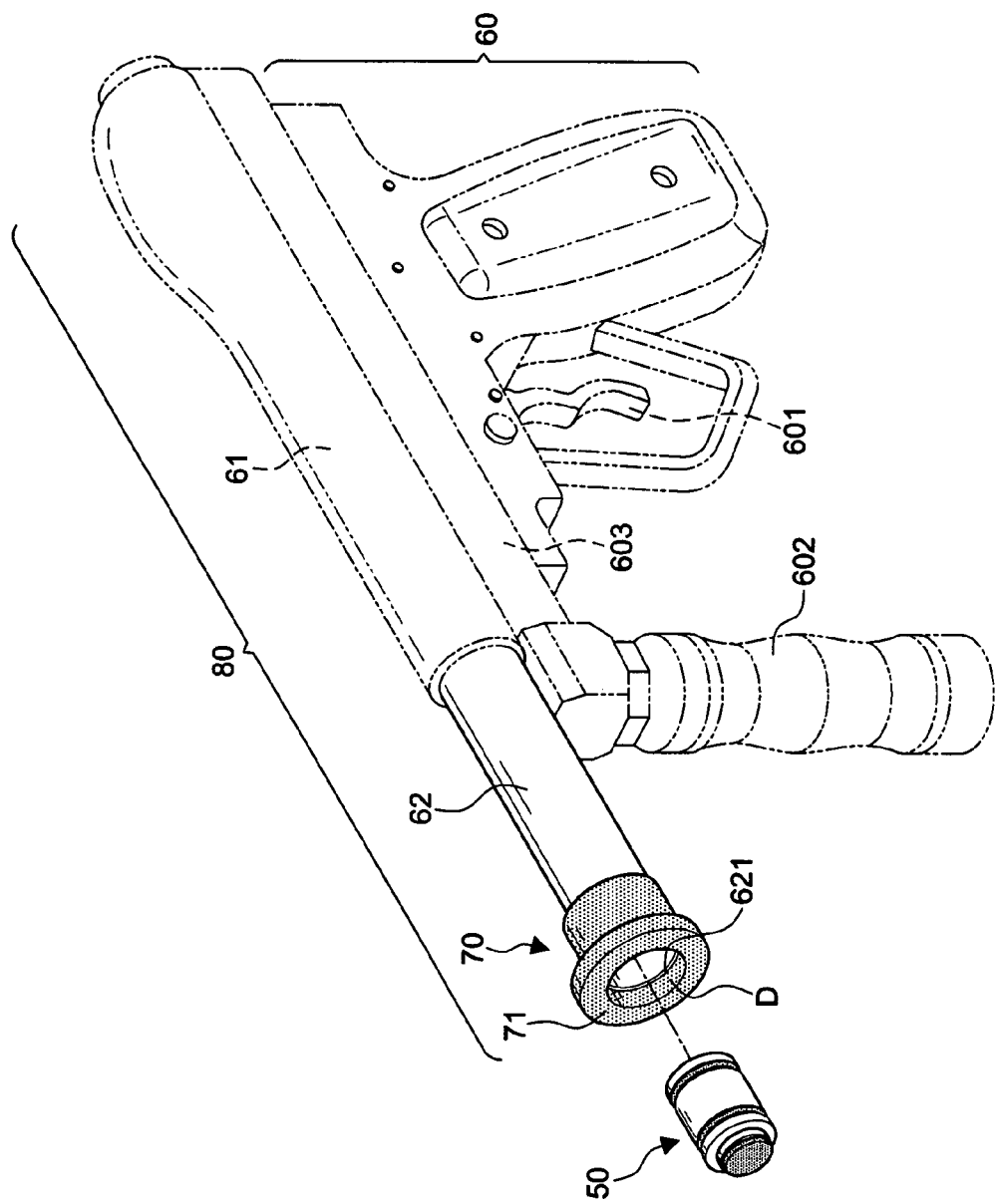
FIG. 5 is a schematic view of a sampling head of the present invention.
Figure 6:
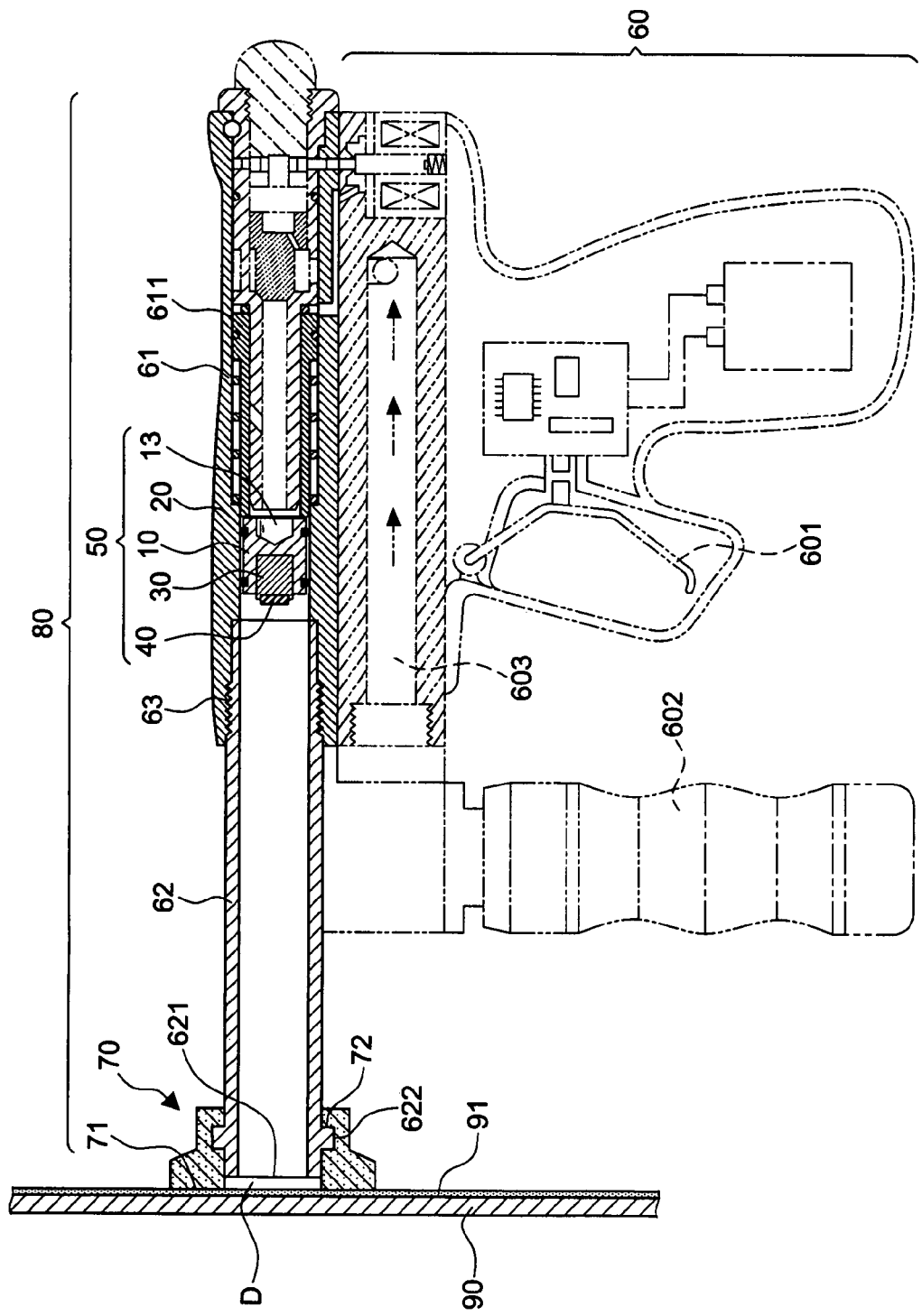
FIG. 6 is a cross-sectional view of a sampling device while a sampling head has not been shot yet in accordance with the present invention.

Referring to FIGS. 5 and 6, the present invention further discloses a sample pushing device 80 for shooting the sampling head 50. The principle and main structure of the sample pushing device 80 are the same as those of a general paintgun, and the sample pushing device 80 is preferably pushed by compressed air. The paintguns of this sort have been disclosed in R.O.C. Pat. Publication Nos. 540689 and 575161 and U.S. Pat. Nos. 6,601,780 and 6,925,997, but not limited to those described in these patents only, and any other pushing mechanism similar to a paintgun or an air gun can be used as a substitute. The present invention adopts a paintgun as the shooting mechanism, because the air pressure of the paintgun is approximately equal to 50 kg/cm2, and the external diameter of a paintball is approximately equal to 17.5 mm, and the radial diameter of the sampling head 50 of the invention is substantially equal to the diameter of the paintball, and the weights of both are about the same. Therefore, if the foregoing paintgun is used for a trial shooting, the present invention only improves the length and the structure of the gun barrel 62, and different parameters including the length of the gun barrel 62 and the weight of the sampling head 50 are used for reference to compute an optimal air pressure value required for shooting, and the air pressure value can be adjusted or set to a constant by the control devices in the gun body 60. The present invention further discloses a sampling device comprising the sampling head 50 and the sample pushing device 80 for shooting the sampling head 50, wherein the sample pushing device 80 is a paintgun that uses air as a driving force and comprises a gun body 60, a shooting barrel 61 and a gun barrel 62. The gun body 60 includes components such as a trigger 601, an air pressure source 602 and an air chamber 603 for controlling the pressure of air entering into the shooting barrel 61, and the shooting barrel 61 contains a pneumatic pushing module 611, and the gun barrel 62 is installed at a front end of the shooting barrel 61. The foregoing components are components of a general paintgun structure, which are prior arts and will not be described further here.

The differences of the sample pushing device 80 of the present invention from the general paintgun reside on that the gun barrel 62 can be shortened, and an elastic positioning disc 70 is sheathed onto the gun muzzle 621 at its front end, and a pressing surface 71 is formed at a front end of the positioning disc 70. In this embodiment, the positioning disc 70 is preferably made of rubber, so that it can have attaching and positioning effects to prevent the gun muzzle 621 from directly contacting the paint surface and provide a buffer function.

Further, the pressing surface 71 is protruded with a distance D from a front end of the gun muzzle 621, and this design can prevent the gun muzzle 621 from directly contacting a substrate such as the steel plate 90 of the vehicle, or can prevent the paint surface 90 from being scraped or damaged.

In this embodiment, the gun barrel 62 and the positioning disc 70 are fixed by installing a circular protruding rib 622 at the external periphery of a gun barrel 62 and proximate to the gun muzzle 621, and a position corresponding to the internal diameter of the positioning disc 70 has a circular groove 72 embedded and fixed onto the gun muzzle 621. The gun barrel 62 can be secured to an outlet of the shooting barrel 61 by a screwing method 63 to facilitate changing the gun barrel 62 with a different length to fit various different requirements, and allow users to remove and store the device without occupying much space.

Figure 7:
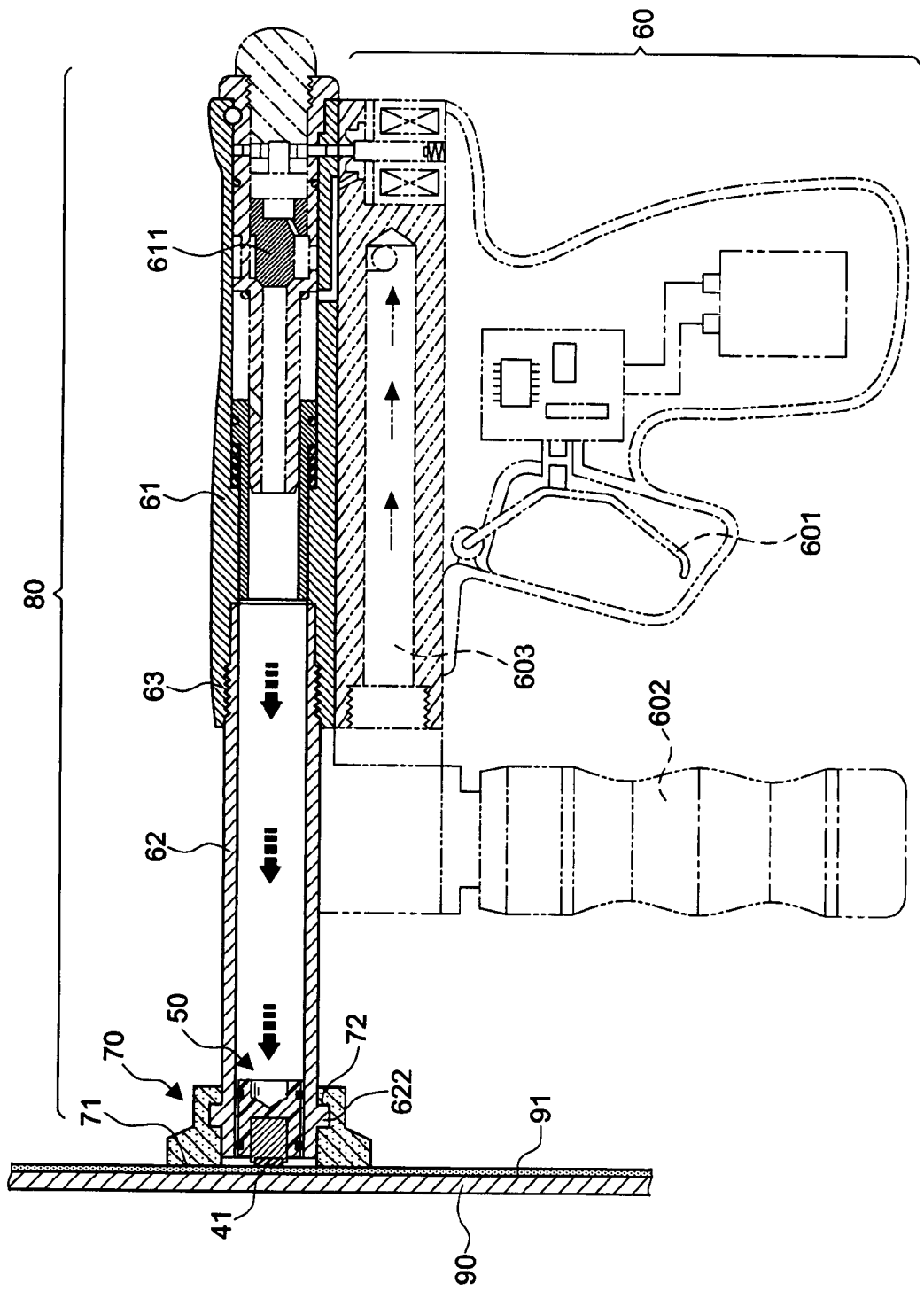
FIG. 7 is a cross-sectional view of a sampling device after a sampling head has been shot at the surface of a vehicle in accordance with the present invention.

Referring to FIG. 6, if it is necessary to collect a sample of paint 91 of a vehicle 90, the sampling head 50 is placed into the shooting barrel 61, and then the positioning disc 70 of a sample pushing device 80 is aimed at and pressed against the sample collecting area, and then the trigger 601 is pulled. An air pressure source 602 enters into the shooting barrel 61 through the air chamber 603, such that the pneumatic pushing module 611 pushes the sampling head 50 to move along the gun barrel 62. In FIG. 7, the gluing surface 41 at a front end of the sampling head 50 hits the paint 91. Since the sampling head 50 is a cylindrical body, and an O-ring 20 is installed at the external periphery of the body 10, and thus the O-ring can be moved quickly like a piston in the gun barrel 62. Since the body 10 is made of an industrial plastic material of an appropriate weight, therefore the body 10 is applicable for driving a general paintgun or air gun, but experiments show that if a front end of the body 10 does not come with a small section of metal head 30, and the sampling head 50 hits the motor vehicle, the body generally made of steel plates will be cracked easily by an instant collision, and thus it is necessary to install a metal head 30 to increase the strength.

Figure 8:
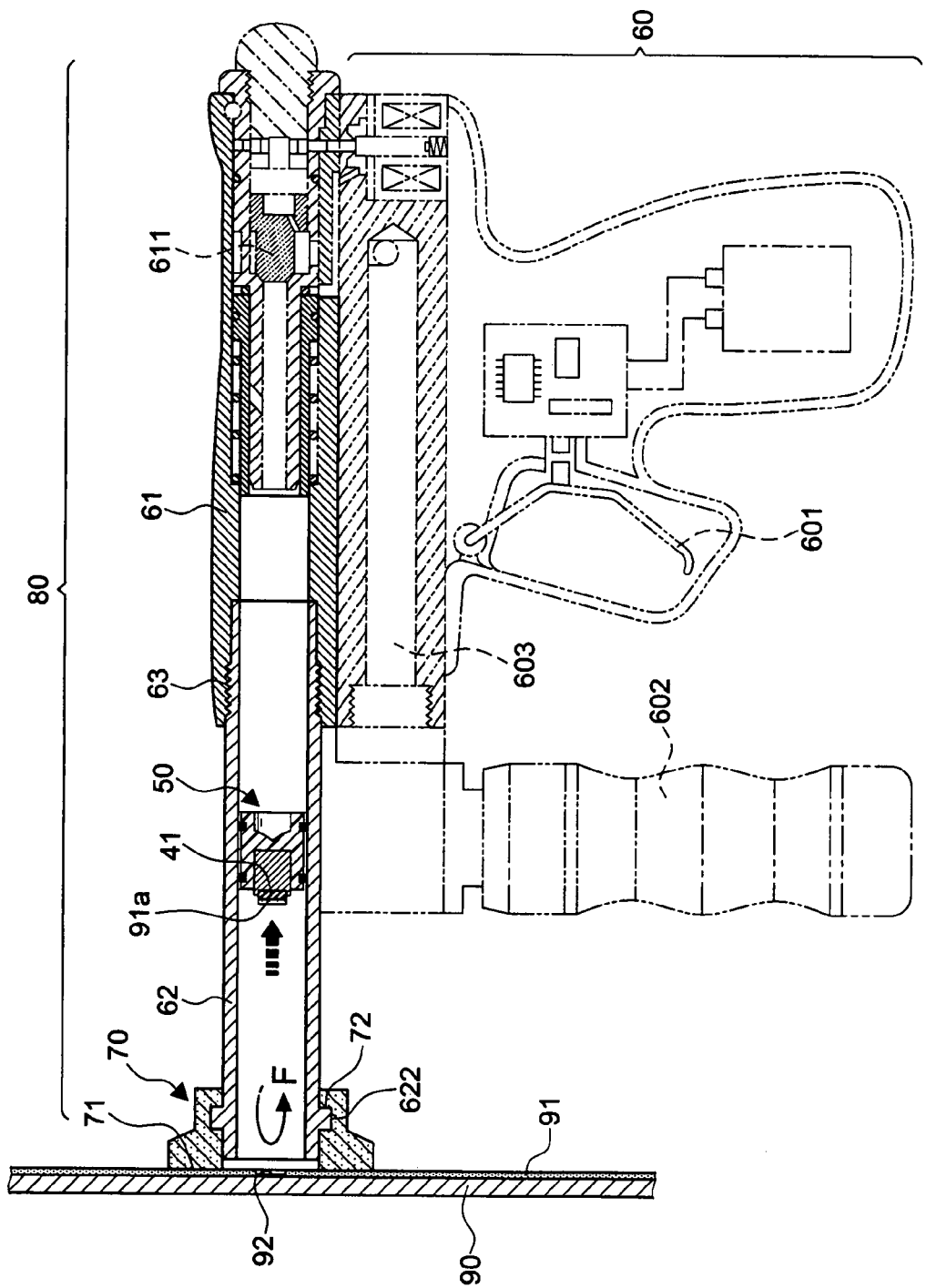
FIG. 8 is a cross-sectional view of a sampling device after a sampling head has been returned in an opposite direction into a gun barrel in accordance with the present invention.

Referring to FIG. 8, the sampling head 50 is shot at the surface of the vehicle 90, and a part of the reaction of the steel plates produced by the instant contact will damage the adhering structure between the paint 91 and the substrate of the car body, and the intact paint chip 91a will fall off easily. Now, the contacted intact paint chip 91a is adhered by the gluing surface 41, such that if the sampling head 50 hits a vehicle to produce a reaction F to force the sampling head 50 to withdraw in an opposite direction from the gun muzzle 621 into the gun barrel 62, and further sucks the intact paint chip 91a from the position of the collision point 92.

Figure 9:
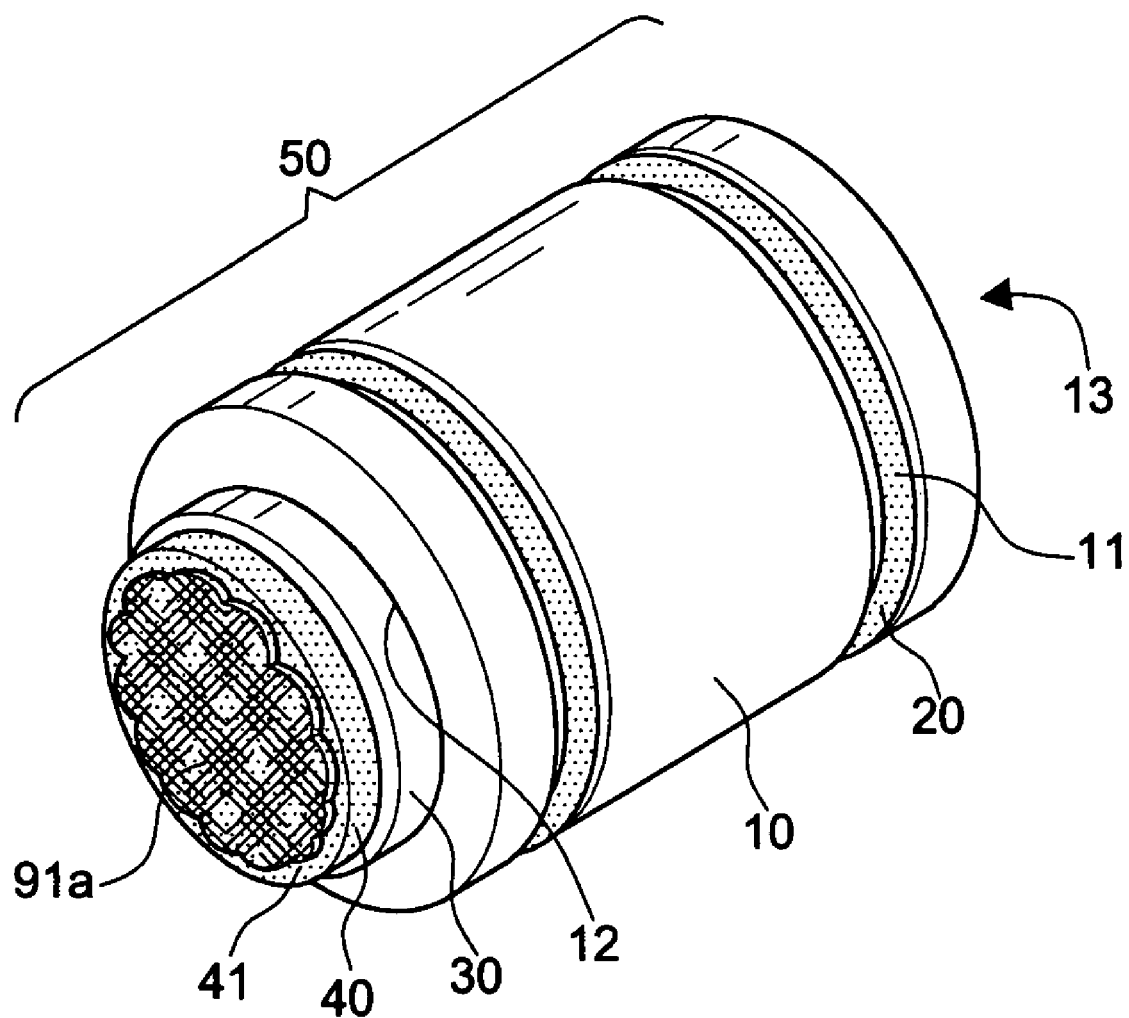
FIG. 9 is a perspective view of a completed sample of the present invention.

In FIG. 9, if the sampling head 50 is removed from the gun barrel 62, the gluing surface 41 will be attached to an intact paint chip 91a of the whole paint layer, and the intact paint chip 91a is in a sheet form and unlike the powder scraped by a common razor blade or in a curled shape. Therefore, the method of the invention can obtain a standard sample for the identification and analysis easily. Therefore, the sampling head 50 of the invention definitely can solve the problems of the sampling by using a razor blade to scrape a paint, so as to achieve the convenience of collecting a sample without damaging the surface of the motor vehicle.

Many changes and modifications in the above-described embodiments of the invention can, of course, be carried out without departing from the scope thereof. Accordingly, to promote the progress in science and the useful arts, the invention is disclosed and is intended to be limited only by the scope of the appended claims.

What is claimed is:

1. A sampling head of a vehicle intact paint chip for forensic applications, comprising:
   a) a body being a non-metal cylindrical body, the body having a circular groove disposed around the external periphery of the body and an installing bore disposed axially at a front end of the body;
   b) at least one O-ring sheathed onto the circular groove and slightly protruded from the surface of the body;
   c) a metal head embedded axially into the installing bore, the metal head having a small portion of the metal head protruded from a front distal surface of the body, a recess being disposed at the front distal surface of the metal head; and
   d) a plastic layer disposed in the recess of the metal head, an external lateral side of the plastic layer being protruded from the front distal surface of the metal head to form a gluing surface for collecting a sample.

2. The sampling head of a vehicle intact paint chip applied for forensic applications as recited in claim 1, wherein the body is made of an industrial plastic material and has a cave disposed at a rear end of the body.

3. The sampling head of a vehicle intact paint chip for forensic applications as recited in claim 1, wherein the plastic layer is made of a foam with a thickness within a range from 1 mm to 4 mm.

4. A sampling device of a vehicle intact paint chip for forensic applications, comprising a pneumatic sample pushing device, having a gun body, a shooting barrel and a gun barrel, and the gun body installs a component therein for controlling the pressure of air that enters into the shooting barrel, and the shooting barrel installs a pneumatic pushing module therein, and the gun barrel is installed at a front end of the shooting barrel; wherein the gun muzzle at a front end of the gun barrel is sheathed with an elastic positioning disc, and a pressing surface is formed at a front end of the positioning disc; and wherein a sampling head, installed in the shooting barrel, and pushed along the gun barrel by the pneumatic pushing module, and comprising:
   a) a body being a non-metal cylindrical body, the body having a circular groove disposed around the external periphery of the body and an installing bore disposed axially at a front end of the body;
   b) at least one O-ring sheathed onto the circular groove and slightly protruded from the surface of the body;
   c) a metal head embedded axially into the installing bore, the metal head having a small portion of the metal head protruded from a front distal surface of the body, a recess being disposed at the front distal surface of the metal head; and
   d) a plastic layer disposed in the recess of the metal head, an external lateral side of the plastic layer being protruded from the front distal surface of the metal head to form a gluing surface for collecting a sample.

5. The sampling device of a vehicle intact paint chip for forensic applications as recited in claim 4, wherein the positioning disc is made of rubber, and the pressing surface is protruded with a distance D from the gun muzzle.

6. The sampling device of a vehicle intact paint chip for forensic applications as recited in claim 4, wherein the gun barrel includes a circular protruding rib disposed at the periphery of the gun barrel and proximate to the gun muzzle, and the internal diameter of the positioning disc includes a circular groove disposed at a corresponding position for embedding and positioning the positioning disc onto the gun muzzle.

7. The sampling device of a vehicle intact paint chip for forensic applications as recited in claim 4, wherein the gun barrel is secured at an outlet of the shooting barrel by a screwing method.

* * * * *